United States Patent
Chen et al.

(10) Patent No.: US 9,222,868 B2
(45) Date of Patent: Dec. 29, 2015

(54) HIGH ACCURACY LIQUID DENSITY SENSOR

(71) Applicant: FINETEK CO., LTD., New Taipei (TW)

(72) Inventors: Jia-Yi Chen, New Taipei (TW); Yung-Long Luo, New Taipei (TW); Wei-Yu Chen, New Taipei (TW); Chao-Kai Cheng, New Taipei (TW)

(73) Assignee: FINETEK CO., LTD., New Taipei (TW)

( * ) Notice: Subject to any disclaimer, the term of this patent is extended or adjusted under 35 U.S.C. 154(b) by 67 days.

(21) Appl. No.: 14/259,130

(22) Filed: Apr. 22, 2014

(65) Prior Publication Data

US 2015/0300935 A1   Oct. 22, 2015

(51) Int. Cl.
| | |
|---|---|
| *G01B 7/14* | (2006.01) |
| *G01N 9/00* | (2006.01) |
| *G01N 9/12* | (2006.01) |
| *G01N 9/14* | (2006.01) |
| *G01N 9/36* | (2006.01) |

(52) U.S. Cl.
CPC ........................................ *G01N 9/36* (2013.01)

(58) Field of Classification Search
CPC ............. G01B 7/14; G01N 9/14; G01N 9/12; G01N 9/00
USPC ..................................................... 324/207.24
See application file for complete search history.

(56) References Cited

U.S. PATENT DOCUMENTS

| 6,408,694 | B1 * | 6/2002 | Lin et al. ......................... 73/444 |
| 2006/0248952 | A1 * | 11/2006 | Jarvie .............................. 73/444 |
| 2007/0282540 | A1 * | 12/2007 | Hart ................................ 702/25 |

* cited by examiner

*Primary Examiner* — Bot Ledynh
(74) *Attorney, Agent, or Firm* — Pai Patent & Trademark Law Firm; Chao-Chang David Pai (57) ABSTRACT

A liquid density sensor has a sensing module, a sensing rod and a floating device. The sensing module has a control circuit having computing functions. The sensing rod has a sensing line electrically connected to the control circuit. The floating device has a first magnetic unit and a floating ball mounted therein. The sensing rod is mounted through the floating device and the floating ball. The floating ball has a second magnetic unit. A specific gravity of the floating ball is lower than that of the floating device. The control circuit calculates a liquid density of liquid based on a distance between the first magnetic unit and the second magnetic unit according to a linear formula.

18 Claims, 9 Drawing Sheets

HIGH ACCURACY LIQUID DENSITY SENSOR

BACKGROUND OF THE INVENTION

1. Field of the Invention

The present invention relates to a liquid density sensor, and more particularly to a high accuracy liquid density sensor.

2. Description of Related Art

Generally, a high-pressure liquid storage device usually comprises a liquid density sensor to sense a density of liquid stored in the high-pressure liquid storage device.

Figure 8:
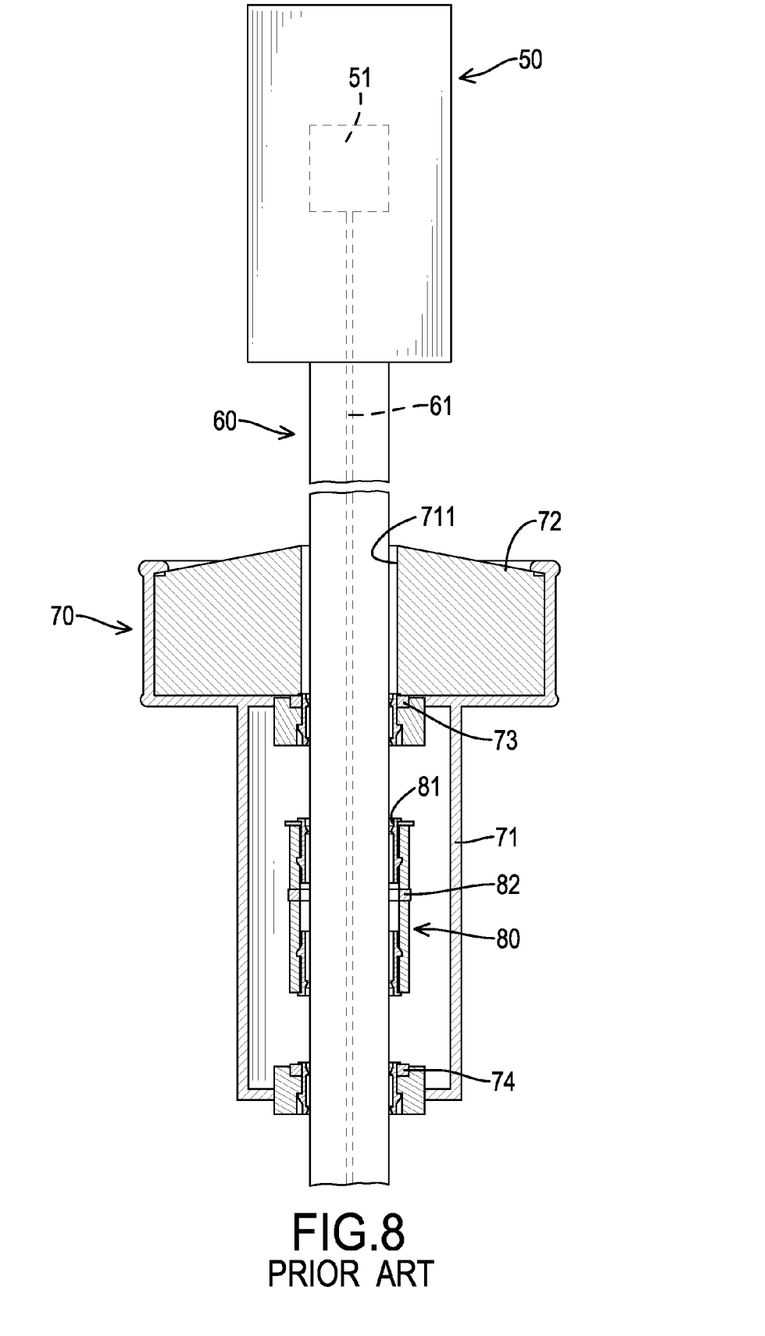
FIG. 8 is a cross-sectional side view of a conventional liquid density sensor.

With reference to FIG. 8, a conventional liquid density sensor comprises a sensing module 50, a sensing rod 60, a first floating ball 70 and a second floating ball 80.

The sensing module 50 has a controller 51 having computing functions.

The sensing rod 60 comprises a hollow tube having two opposite openings and a sensing line 61 mounted in the hollow tube, wherein one end of the sensing line 61 is connected to the controller 51 of the sensing module 50. The first floating ball 70 has a housing 71, a floating part 72, a first magnetic unit 73 and a second magnetic unit 74. The housing 71 has a first opening 711, wherein the sensing rod 60 is mounted through the first opening 711. Thus, the first floating ball 70 is sleeved on the sensing rod 60 and can move in an axial direction of the sensing rod 60. The floating part 72 is mounted in the housing 71 and near the sensing module 50 such that the first floating ball 70 floats on a surface of the liquid. The first magnetic unit 73 and the second magnetic unit 74 are mounted in the housing 71 and around the sensing rod 60, wherein the first magnetic unit 73 is proximal to the floating part 72, and the second magnetic unit 74 is distal from the floating part 72.

The second floating ball 80 is mounted in the housing 71 of the first floating ball 70 and around the sensing rod 60, and comprises a second opening 81 and a third magnetic unit 82. The second floating ball 80 can move in the axial direction of the sensing rod 60. The third magnetic unit 82 is mounted around the sensing rod 60 and between the first magnetic unit 73 and the second magnetic unit 74. Two magnetic poles of the third magnetic unit 82 respectively face the first magnetic unit 73 and the second magnetic unit 74, wherein the third magnetic unit 82 repels both the first magnetic unit 73 and the second magnetic unit 74 to prevent the third magnetic unit 82 being attracted by the first magnetic unit 73 or the second magnetic unit 74 while moving along the axial direction of the sensing rod 60.

When the conventional liquid density sensor is in use, the sensing rod 60 is immersed in the liquid with the sensing module 50 exposed out of the liquid. Since the first magnetic unit 73 is mounted near the floating part 72, the first magnetic unit 73 can be horizontally aligned with the surface of the liquid. The controller 51 of the sensing module 50 outputs a pulse signal to the sensing line 61. When the pulse signal passes a position at which the first magnetic unit 73 is disposed, an induced signal is generated at the position due to a magnetic field of the first magnetic unit 73. When the controller 51 receives the induced signal, the position of the first magnetic unit 73 can be located based on a time difference between outputting the pulse signal and receiving the induced signal, thereby further calculating a liquid level of the liquid.

Furthermore, the liquid will flow into the housing 71 through the first openings 711. The second floating ball 80 will stay at a position between the first magnetic unit 73 and the second magnetic unit 74 due to a force balance among the buoyant force, weight of the second floating ball 80 (gravity), and magnetic repulsion between the third magnetic unit 82, the first magnetic unit 73 and the second magnetic unit 74. The controller 51 can respectively obtain positions of the first magnetic unit 73, the second magnetic unit 74 and the third magnetic unit 82 by using the pulse signal as disclosed above, and further obtain a distance between the first magnetic unit 73 between the third magnetic unit 82, and a distance between the second magnetic unit 74 and the third magnetic unit 82. Then, the controller 51 can obtain a density of the liquid based on the obtained distances.

Figure 9:
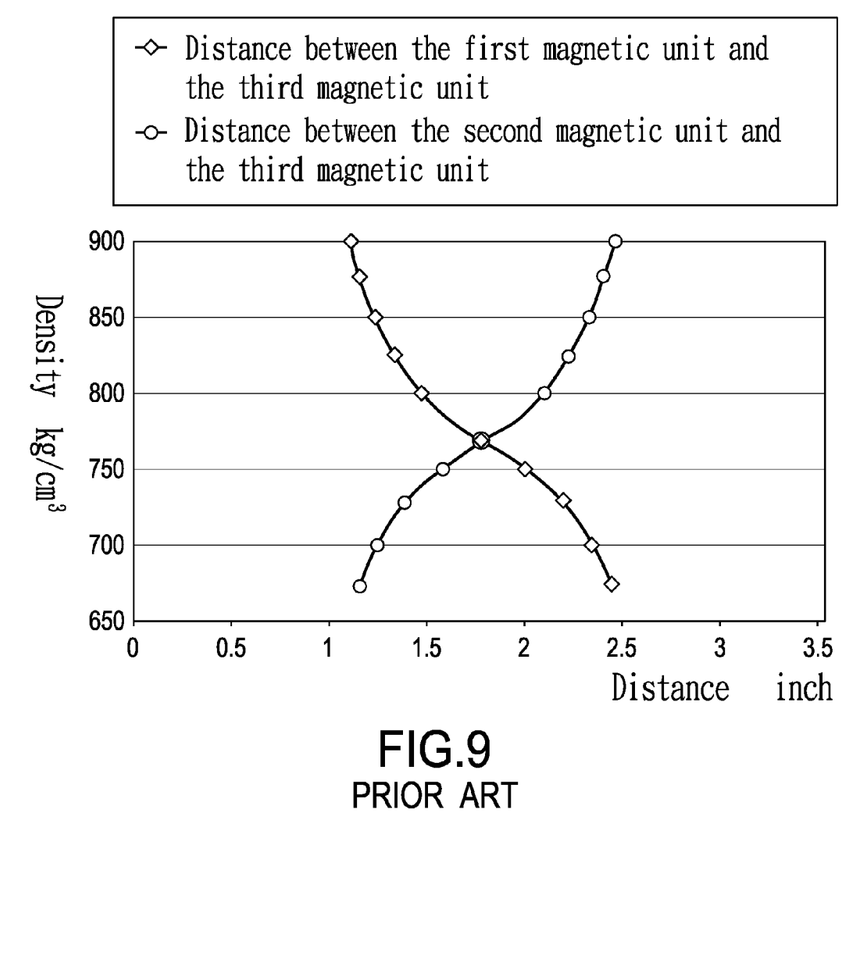
FIG. 9 shows a characteristic curve of the liquid density sensor in FIG. 8.

With further reference to FIG. 9, a vertical axis represents the density of the liquid (kilogram/cubic centimeter), and a horizontal axis represents the distances between the third magnetic unit 82, the first magnetic unit 73 and the second magnetic unit 74 (inches). If the liquid has a relative high density, the second floating ball 80 goes up due to an increasing of the buoyant force, thus, the third magnetic unit 82 approaches the first magnetic unit 73 and leaves the second magnetic unit 74. On the contrary, if the liquid has a relative low density, the second floating ball 80 goes down due to a decreasing of the buoyant force, thus, the third magnetic unit 82 leaves the first magnetic unit 73 and approaches the second magnetic unit 74. The controller 51 calculates the density of the liquid based on two characteristic curves shown in FIG. 9.

However, the third magnetic unit 82 repels both the first magnetic unit 73 and the second magnetic unit 74, and thus, the two characteristic curves shown in FIG. 9 are both nonlinear. Calculations of nonlinear characteristic curves are very difficult and complicated, that is, the density of the liquid must be calculated through complex calculations, otherwise calculation errors easily occur and decrease accuracy of the sensing result.

SUMMARY OF THE INVENTION

The main objective of the invention is to provide a high accuracy liquid density sensor. The high accuracy liquid density sensor comprises a sensing module, a sensing rod and a floating device.

The sensing module has a control circuit capable of executing computing functions.

The sensing rod has a first end adapted to be immersed in liquid, and a second end to be mounted to the sensing module, wherein the sensing rod comprises a hollow tube and a sensing line that is mounted in the hollow tube and is electrically connected to the control circuit.

The floating device comprises a housing, a first magnetic unit and a floating ball.

The housing has two opposite first openings formed through the housing, wherein the sensing rod is mounted through the two opposite first openings, and the at least one floating device is movable along the sensing rod; and at least one side hole is formed through the housing.

The first magnetic unit is mounted in the housing and at a side away from the sensing module.

The floating ball has a specific gravity lower than that of the housing. The floating ball is movably mounted around the sensing rod and in the housing, and has a second magnetic unit mounted therein at an end distal from the first magnetic unit.

The control circuit obtains a location of the first magnetic unit on the sensing line and a location of the second magnetic unit on the sensing line respectively, and calculates a distance between the first magnetic unit and the second magnetic unit.

When the high accuracy liquid density sensor in accordance with the present invention is in use, the first end of the sensing rod is immersed in the liquid. The liquid flows in the floating device via the at least one side hole, thus, the floating device and the floating ball both float on a surface of the liquid. The first magnetic unit and the second magnetic unit are located at different heights, and the distance between the first magnetic unit and the second magnetic unit is linear with a liquid density of the liquid. Therefore, the control circuit can calculate the liquid density based on the distance between the first magnetic unit and the second magnetic unit through linear equations, and an accuracy of the sensing result can be increased.

DETAILED DESCRIPTION OF THE PREFERRED EMBODIMENTS

Figure 1:
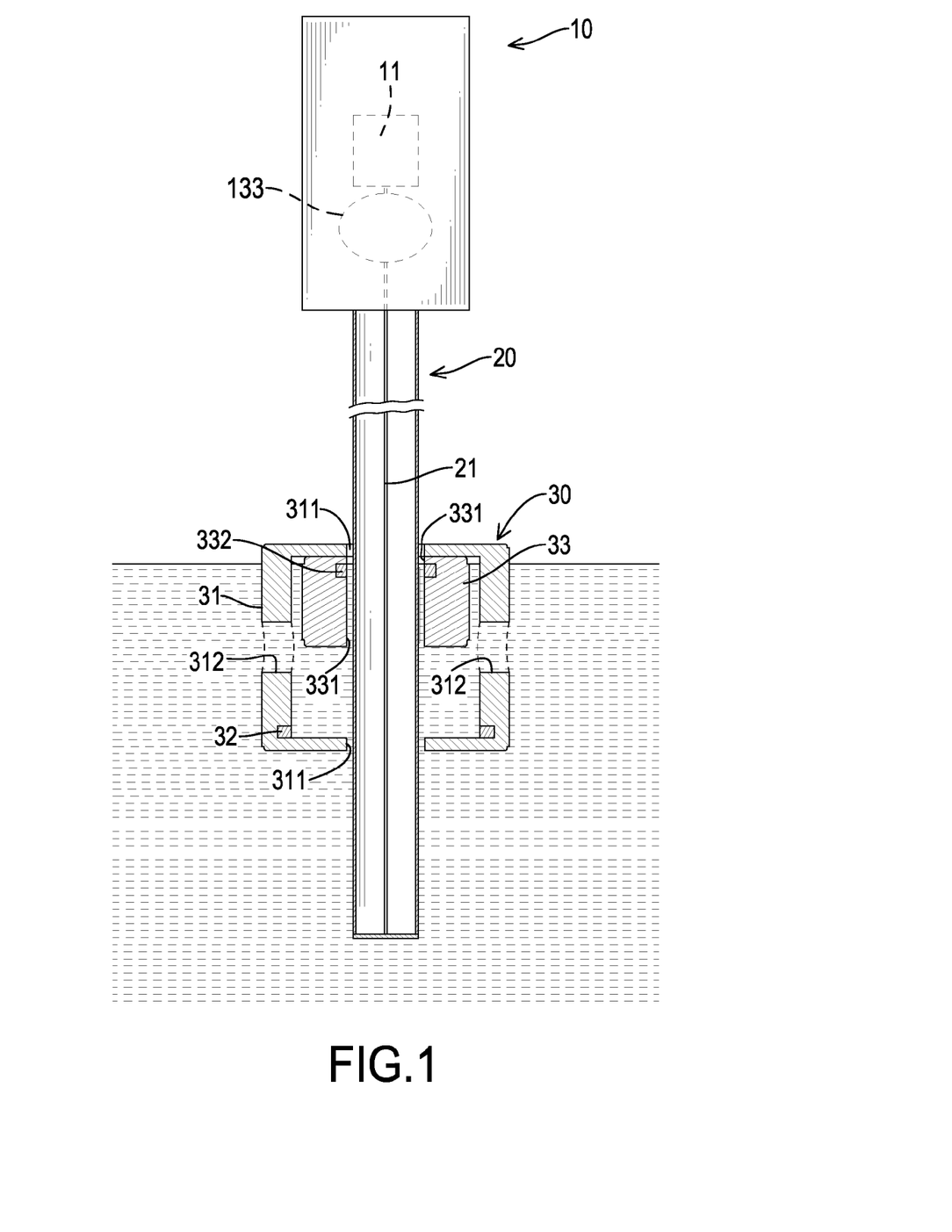
FIG. 1 is a cross-sectional view of a first preferred embodiment of a high accuracy liquid density sensor in accordance with the present invention.
Figure 2:
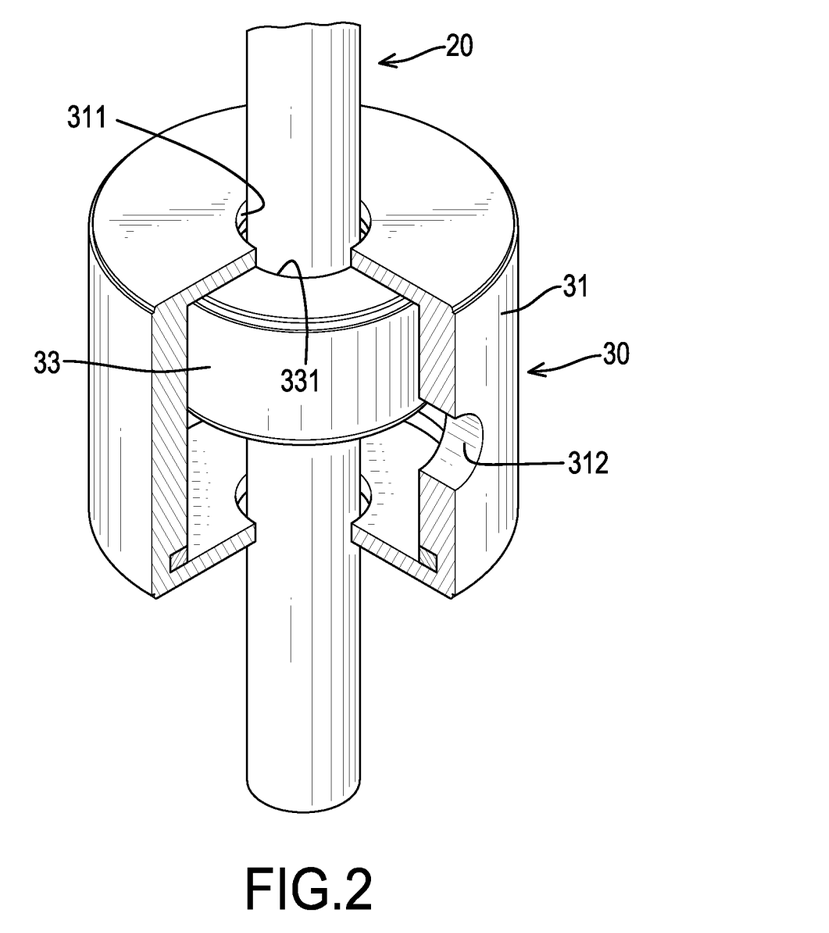
FIG. 2 is a perspective cross-sectional view of the high accuracy liquid density sensor in FIG. 1.

With reference to FIGS. 1 and 2, a first preferred embodiment of a high accuracy liquid density sensor in accordance with the present invention comprises a sensing module 10, a sensing rod 20 and a floating device 30.

The sensing module 10 has a control circuit 11 having computing functions.

The sensing rod 20 comprises a hollow tube and a sensing line 21. One end of the hollow tube is connected to the sensing module 10, and the other end of the hollow tube is to be immersed in liquid. The sensing line 21 is mounted in the sensing rod 20 and electrically connected to the control circuit 11 of the sensing module 10.

The floating device 30 comprises a housing 31, a first magnetic unit 32 and a floating ball 33.

The housing 31 has two opposite first openings 311 and two side holes 312, wherein the sensing rod 20 is mounted through the two first openings 311, and the floating device 30 can move along the sensing rod 20. The first magnetic unit 32 is mounted in the housing 31 and at a side away from the sensing module 10. In this embodiment, the first magnetic unit 32 is mounted on an inner bottom surface of the housing 31.

The floating ball 33 is mounted in the floating device 30, and has two opposite second openings 331 and a second magnetic unit 332. The sensing rod 20 is mounted through the two second openings 331, and the floating ball 33 can move in the axial direction of the sensing rod 20. The second magnetic unit 332 is mounted in the floating ball 33 and is at an end distal from the first magnetic unit 32 of the floating device 30. A specific gravity of the floating ball 33 is lower than a specific gravity of the housing 31.

In the first preferred embodiment, the floating ball 33 is made of a foam material. The first magnetic unit 32 and the second magnetic unit 332 are made of material comprising nickel (Ni), cobalt (Co) or iron (Fe). Shapes of the first magnetic unit 32 and the second magnetic unit 332 can be annular, cylindrical, cube or irregular.

Figure 3:
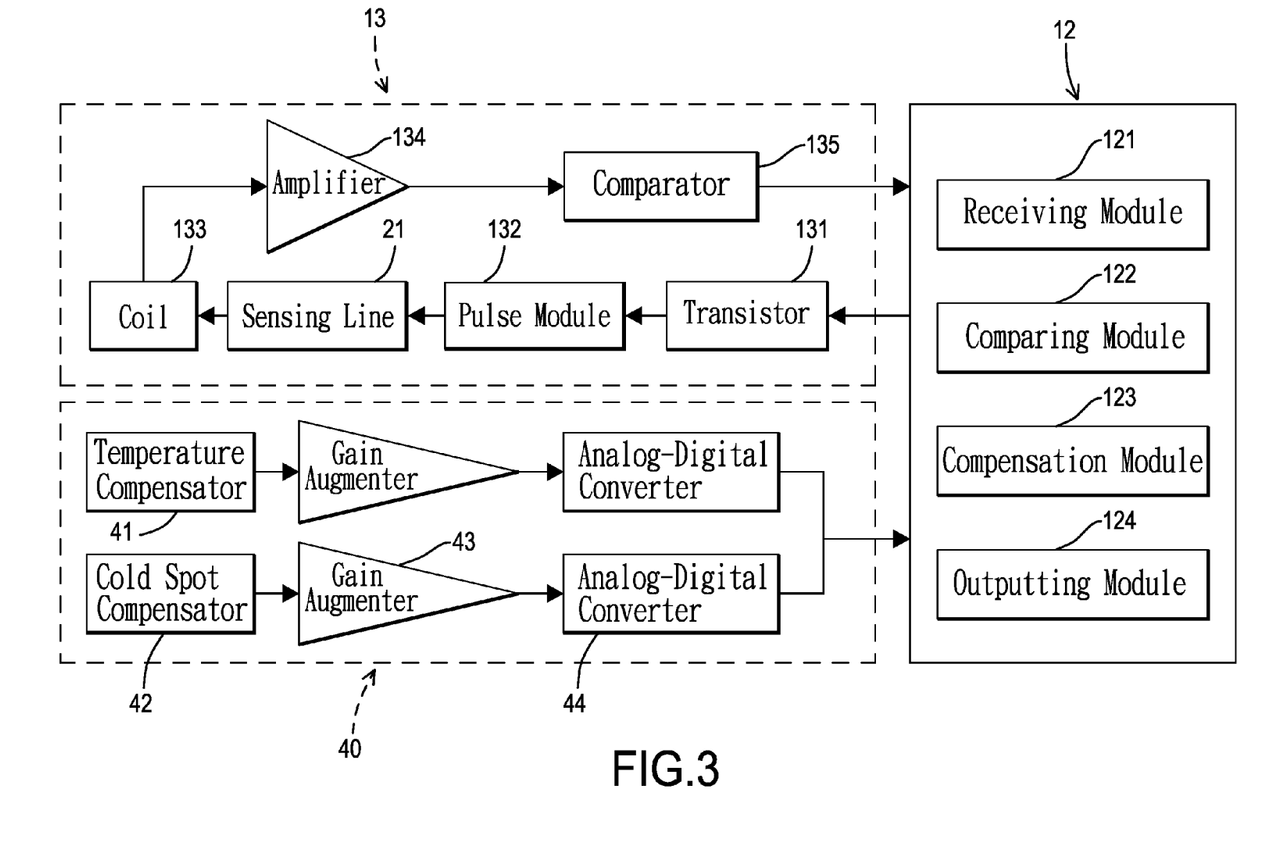
FIG. 3 is a circuit diagram of a control circuit of the high accuracy liquid density sensor in FIG. 1.

With reference to FIG. 3, in the first preferred embodiment, the control circuit 11 of the sensing module 10 comprises an internal circuit 12 and an external circuit 13, wherein the external circuit 13 is electrically connected to the sensing line 21 of the sensing rod 20.

The internal circuit 12 is electrically connected to the sensing line 21 via the external circuit 13. The internal circuit 12 has a receiving module 121, a comparing module 122 and an outputting module 124. The receiving module 121 receives a first induced signal and a second induced signal from the external circuit 13. The comparing module 122 is electrically connected to the receiving module 121 to obtain the first induced signal and the second induced signal, and then calculates a liquid level and a liquid density of the liquid based on the first induced signal and the second induced signal. When the liquid density sensor of the present invention is turned on, the outputting module 124 outputs a trigger signal to the external circuit 13.

The external circuit 13 is electrically connected to the internal circuit 12 and the sensing line 21. The external circuit 13 has a transistor 131, a pulse module 132, a coil 133, an amplifier 134 and a comparator 135. The transistor 131 is electrically connected to the pulse module 132 and the outputting module 124, wherein the transistor 131 is used as a switch. When the transistor 131 receives the trigger signal, the transistor 131 drives the pulse module 132 to output a pulse signal to the sensing line 21. In the first preferred embodiment, the transistor 131 is a MOSFET.

When the pulse signal passes through a first location on the sensing line 21 where the first magnetic unit 32 is disposed, the first induced signal is generated at the first location due to an electromagnetic induction between the pulse signal and the first magnetic unit 32. When the pulse signal passes through a second location on the sensing line 21 where the second magnetic unit 332 is disposed, the second induced signal is generated at the second location due to an electromagnetic induction between the pulse signal and the second magnetic unit 332. A transmission speed of the first induced signal equals a transmission speed of the second induced signal.

The coil 133 is mounted on the sensing line 21 and near an end distal from the sensing module 10. The coil 133 is electrically connected to the sensing line 21 to receive the first induced signal and the second induced signal.

The amplifier 134 is electrically connected to the coil 133 to obtain and amplify the first induced signal and the second induced signal.

The comparator 135 is electrically connected to the amplifier 134 to obtain the amplified first induced signal and the amplified second induced signal, wherein the comparator 135 converts the amplified first induced signal and the amplified second induced signal from analog forms to digital forms, and outputs the converted first induced signal and the converted second induced signal to the internal circuit 12.

Figure 4A:
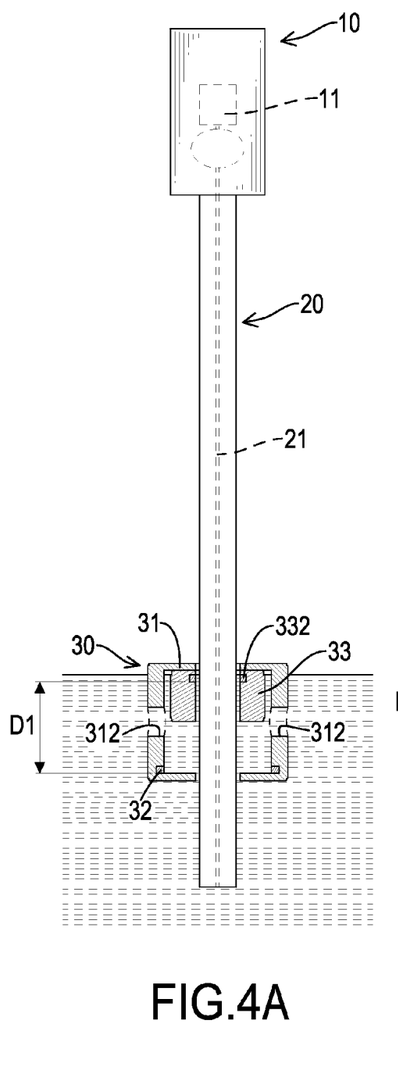
FIG. 4A is an operational cross-sectional side view of the high accuracy liquid density sensor in FIG. 1.
Figure 5A:
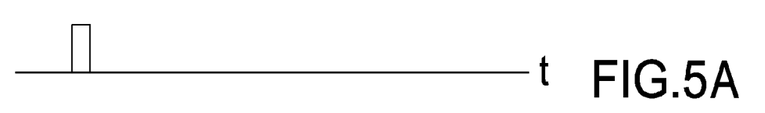
FIGS. 5A to 5C are output waveform charts corresponding to FIG. 4A.
Figure 5B:
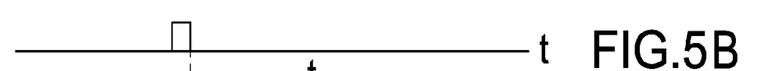
Figure 5C:
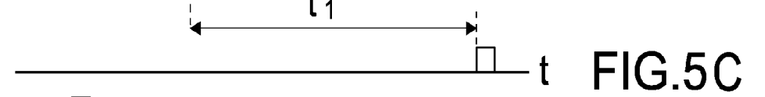

With reference to FIG. 4A and corresponding FIGS. 5A to 5C, FIG. 5A represents the pulse signal output from the pulse module 132, FIG. 5B represents the second induced signal resulted from the second magnetic unit 332 shown in FIG. 4A, and FIG. 5C represents the first induced signal resulted from the first magnetic unit 32 shown in FIG. 4A.

Figure 4B:
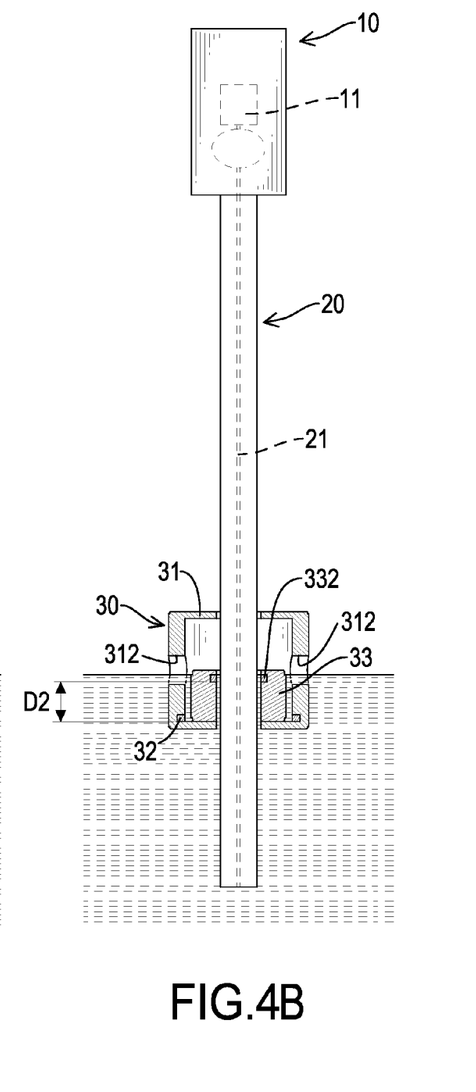
FIG. 4B is another operational cross-sectional side view of the high accuracy liquid density sensor in FIG. 1.
Figure 5D:
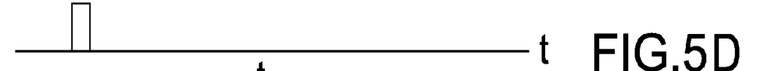
FIGS. 5D to 5F are output waveform charts corresponding to FIG. 4B.
Figure 5E:
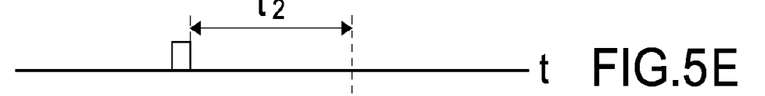
Figure 5F:
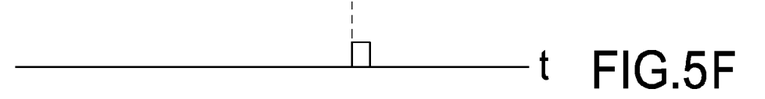

FIG. 4B and corresponding FIGS. 5D to 5F, FIG. 5D represent the pulse signal outputs from the pulse module 132, FIG. 5E represents the second induced signal resulted from the second magnetic unit 332 shown in FIG. 4B, and FIG. 5C represents the first induced signal resulted from the first magnetic unit 32 shown in FIG. 4B. All horizontal axes in FIGS. 5A to 5F represent time.

Figure 6:
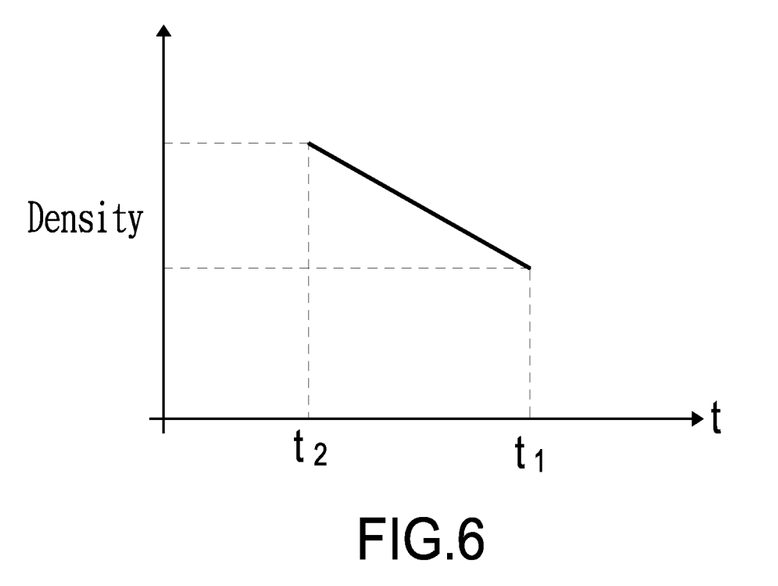
FIG. 6 shows a characteristic curve of the high accuracy liquid density sensor in FIG. 1.

With reference to FIG. 6, an inverse relationship between a liquid density of the liquid and a time difference t1, t2 between receiving of the first induced signal and receiving of the second induced signal is shown. The higher the liquid density is, the lower the time difference is.

When the high accuracy liquid density sensor of the present invention is in use, the sensing rod 20 is dipped into the liquid with the sensing module 10 exposed out of the liquid. The floating device 30 floats on a surface of the liquid, wherein a dipped depth of the floating device 30 depends on the liquid density of the liquid. Besides, the liquid flows into the floating device 30 via the two side holes 312 until a level of the liquid inside the floating device 30 equals a level of the liquid outside the floating device 30. The floating ball 33 thus floats on the surface of the liquid in the floating device 30.

When the floating device 30 and the floating ball 33 both stop moving, the outputting module 124 of the internal circuit 12 outputs the trigger signal to the transistor 131 of the external circuit 13. Then, the transistor 131 drives the pulse module 132 to output the pulse signal to the sensing line 21. When the pulse signal passes through the first location corresponding to the first magnetic unit 32, the first induced signal is generated. When the pulse signal passes through the second location corresponding to the second magnetic unit 332, the second induced signal is generated. Then, the coil 133 receives the first induced signal and the second induced signal. The amplifier 134 obtains and amplifies the first induced signal and the second induced signal. The comparator 135 converts the amplified first induced signal and the amplified second induced signal from analog forms to digital forms.

After that, the receiving module 121 receives the first induced signal and the second induced signal from the external circuit 13, and the comparing module 122 obtains the first induced signal and the second induced signal, and then calculates the liquid density of the liquid based on the first induced signal and the second induced signal.

Details of calculating the liquid density of the liquid based on the time difference between receiving of the first induced signal and receiving of the second induced signal are introduced as follows.

By observing FIGS. 4A and 4B, the liquid levels of two different kinds of liquid shown in the two examples are the same. A first distance between the first magnetic unit 32 and the second magnetic unit 332 in FIG. 4A is d1, and a second distance between the first magnetic unit 32 and the second magnetic unit 332 in FIG. 4B is d2.

Because the floating ball 33 is lower than the floating device 30 in specific gravity, the second magnetic unit 332 is horizontally aligned with the surface of the liquid, while the first magnetic unit 32 of the floating device 30 may be immersed in different depths, depending on the liquid density of the liquid. If the liquid has a higher liquid density, the immersed depth of the floating device 30 is low due to the high buoyancy of the floating device 30, and then the distance between the first magnetic unit 32 and the second magnetic unit 332 is short as shown in FIG. 4B.

With further observance of FIGS. 4A and 4B, the distance d1 between the first magnetic unit 32 and the second magnetic unit 332 in FIG. 4A is longer than the distance d2 between the first magnetic unit 32 and the second magnetic unit 332 in FIG. 4B, that is, the liquid density of the liquid in FIG. 4A is lower than the density of the liquid in FIG. 4B.

With reference to FIGS. 5A to 5F, the pulse signals shown in FIGS. 5A and 5D are outputted simultaneously. The two second magnetic units 332 in FIGS. 4A and 4B stay at the same height such that the second induced signals shown in FIGS. 5B and 5E are also simultaneously generated. Only the height of the first magnetic unit 32 in FIG. 4A and the height of the first magnetic unit 32 in FIG. 4B are different due to the different densities of the liquids in FIG. 4A and in FIG. 4B. The first induced signal shown in FIG. 5C and the first induced signal shown in FIG. 5F are thus not outputted simultaneously, wherein the first induced signal shown in FIG. 5C is generated later than the first induced signal shown in FIG. 5F.

In FIGS. 5B, 5C, 5E and 5F, a time difference t1 is longer than a time difference t2. A distance between the first magnetic unit 32 and the second magnetic unit 332 is linear with and proportional to the time difference. Thus, the comparing module 122 of the internal circuit 12 can calculate the liquid density of the liquid based on the time difference.

Furthermore, the location of the second magnetic unit 332 is horizontally aligned with the surface of the liquid, that is, the height of the second magnetic unit 332 equals the liquid level of the liquid. Therefore, the comparing module 122 of the internal circuit 12 also can calculate the liquid level of the liquid based on the time difference between outputting of the pulse signal and receiving of the second induced signal.

With further observance of FIGS. 4A and 4B, the floating ball 33 in FIG. 4A is located near the sensing module 10. When the liquid density of the liquid shown in FIG. 4A further decreases, the floating device 30 would further sink and push the floating ball 33 under the surface of the liquid, and that would eventually cause an error sensing result. In conclusion, FIG. 4A shows a tolerable lowest density that can be sensed by the liquid density sensor.

When the density of the liquid shown in FIG. 4B increases, the floating device 30 would further go up and lift the floating ball 33 above the surface of the liquid, and that would cause an error sensing result. In conclusion, FIG. 4B shows a tolerable highest density that can be sensed by the liquid density sensor.

The liquid density sensor of the present invention is adapted for sensing liquid having a liquid density between the lowest density and the highest density as described above. With reference to FIG. 6, a distance between the first magnetic unit 32 and the second magnetic unit 332 is linear with and proportional to a time difference between receiving of the first induced signal and receiving of the second induced signal. The time difference t1 corresponds to the lowest density, and the time difference t2 corresponds to the highest density. When the liquid density sensor senses another kind of liquid having liquid density ranging between the lowest density and the highest density, the liquid density sensor obtains a time difference t (t1<t<t2). The liquid density corresponding to the time difference t can be calculated by a simple linear formula:

$$\text{The highest density} + \frac{t \times (\text{the lowest density} - \text{the highest density})}{t1 - t2}$$

Comparing to the conventional nonlinear curve, the simple linear formula of the present invention facilitates easy calculation of the liquid density.

In addition, temperature of the liquid may influence a volume of the liquid. Generally, when the temperature rises, the volume of the liquid expands and the liquid level rises. When the temperature decreases, the volume of the liquid shrinks and the liquid level drops. Therefore, storage of the liquid is hard to be estimated, thus, a standard temperature (for example, 25 degrees Celsius) is formulated, and the liquid level of the liquid at the standard temperature is identified as a standard level of the liquid.

With reference to FIG. 3, in a second preferred embodiment of the control circuit 11, the control circuit 11 further comprises a temperature module 40, and the internal circuit 12 further comprises a compensation module 123.

The temperature module 40 has a temperature compensator 41, a cold spot compensator 42, two gain augmenters 43 and two analog-digital converters 44. The temperature compensator 41 and the cold spot compensator 42 are electrically connected to the two gain augmenters 43 respectively, wherein the two gain augmenters 43 are electrically connected to the two analog-digital converters 44 respectively.

The temperature compensator 41 senses the temperature of the liquid and outputs a temperature signal based on the sensed temperature to the compensation module 123 of the internal circuit 12. The cold spot compensator 42 senses the temperature of the liquid and outputs a cold spot signal based on the temperature to the compensation module 123 of the internal circuit 12. The compensation module 123 outputs a compensation signal to the comparing module 122. When the temperature is higher than the standard temperature, the comparing module 122 decreases the value of the liquid level based on the compensation signal. When the temperature is lower than the standard temperature, the comparing module 122 increases the value of the liquid level based on the compensation signal. In conclusion, the temperature module 40 and the compensation module 123 adjust the value of the liquid level according to the standard temperature.

Figure 7A:
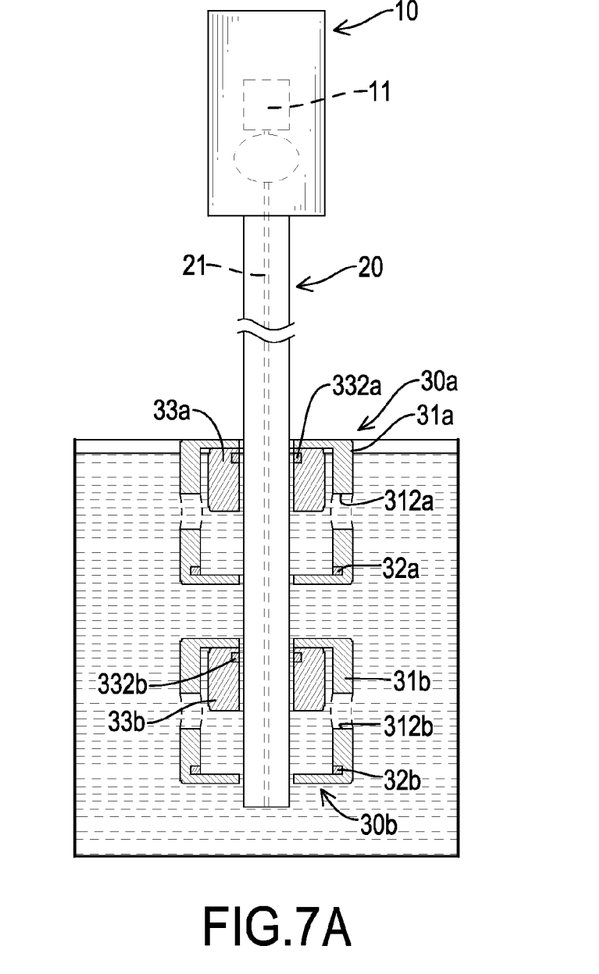
FIG. 7A is an operational cross-sectional side view of a second preferred embodiment of a high accuracy liquid density sensor in accordance with the present invention.

Furthermore, with reference to FIG. 7A, a second preferred embodiment of the high accuracy liquid density sensor in accordance with the present invention comprises a sensing module 10, a sensing rod 20, a first floating device 30a, and a second floating device 30b. The second preferred embodiment may be used for sensing a biphasic liquid including a first liquid L1 and a second liquid L2.

The floating device 30a is located at a first junction between the air and the first liquid L1, and the second floating device 30b is located at a second junction between the first liquid L1 and the second liquid L2.

Figure 7B:
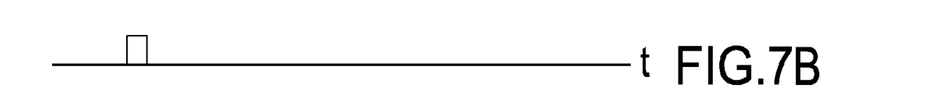
FIGS. 7B to 7D are output waveform charts corresponding to FIG. 7A.
Figure 7C:
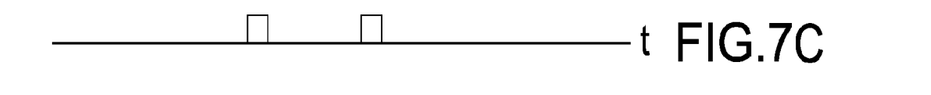
Figure 7D:
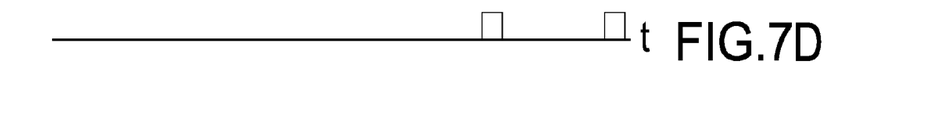

FIG. 7B represents a pulse signal. FIG. 7C represents induced signals of the first floating device 30a located at the first junction between the air and the first liquid. FIG. 7D represents induced signals of the second floating device 30b located at the second junction between the first liquid and the second liquid.

The induced signals shown in FIG. 7C from left to right are sequentially a second induced signal and a first induced signal of the first floating device 30a. The control circuit 11 can calculate a first liquid density of the first liquid based on a time difference between receiving of the first induced signal and receiving of the second induced signal of the first floating device 30a. Besides, the control circuit 11 can further calculate a liquid level of the first liquid based on a time difference between outputting of the pulse signal and receiving of the second induced signal of the first floating device 30a.

The induced signals shown in FIG. 7D from left to right are sequentially a second induced signal and a first induced signal of the second floating device 30b. The control circuit 11 calculates a second liquid density of the second liquid based on a time difference between receiving of the first induced signal and receiving of the second induced signal of the second floating device 30b 1. Besides, the control circuit 11 can further calculate a level of the second liquid based on a time difference between outputting of the pulse signal and receiving of the second induced signal of the second floating device 30b.

In conclusion, the liquid density sensor can be adapted for sensing densities and levels of liquid having multiple levels by using multiple floating devices 30a, 30b.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A high accuracy liquid density sensor comprising:
   a sensing module having a control circuit capable of executing computing functions;
   a sensing rod adapted to be partially immersed in liquid, wherein the sensing rod comprises
      a hollow tube; and
      a sensing line mounted in the hollow tube and electrically connected to the control circuit of the sensing module; and
   at least one floating device comprising
      a housing having
         two opposite first openings formed through the housing, wherein the sensing rod is mounted through the two opposite first openings, and the at least one floating device is movable along the sensing rod; and
         at least one side hole formed through the housing;
      a first magnetic unit mounted in the housing and at a side away from the sensing module; and
      a floating ball mounted around the sensing rod and in the housing, and being movable along the sensing rod and having
   a second magnetic unit mounted in the floating ball and at an end distal from the first magnetic unit;
      wherein a specific gravity of the floating ball is lower than a specific gravity of the at least one floating device;
   wherein the control circuit obtains a location of the first magnetic unit on the sensing line and a location of the second magnetic unit on the sensing line respectively, and calculates a distance between the first magnetic unit and the second magnetic unit; and
   the distance between the first magnetic unit and the second magnetic unit is linear with a liquid density of a liquid, and the control circuit calculates the liquid density of the liquid based on the distance between the first magnetic unit and the second magnetic unit.

2. The liquid density sensor as claimed in claim 1, wherein the control circuit obtains a liquid level of the liquid based on the location of the second magnetic unit on the sensing line.

3. The liquid density sensor as claimed in claim 1 comprising multiple floating devices, wherein specific gravities of the multiple floating devices are different, and the floating device relatively closer to the sensing module has the specific gravity higher than the specific gravity of another floating device relatively far away from the sensing module;
   wherein specific gravities of the floating balls in the multiple floating devices are different, and the floating ball relatively closer to the sensing module has the higher specific gravity than the specific gravity of another floating ball far away from the sensing module.

4. The liquid density sensor as claimed in claim 2 comprising multiple floating devices, wherein specific gravities of the multiple floating devices are different, and the floating device relatively closer to the sensing module has the specific gravity higher than the specific gravity of another floating device relatively far away from the sensing module;

wherein specific gravities of the floating balls in the multiple floating devices are different, and the floating ball relatively closer to the sensing module has the higher specific gravity than the specific gravity of another floating ball far away from the sensing module.

5. The liquid density sensor as claimed in claim 2, wherein the control circuit calculates the liquid density of the liquid through steps of:

outputting a pulse signal to the sensing line of the sensing rod to induce a first induced signal and a second induced signal respectively corresponding to the first magnetic unit and the second magnetic unit, wherein the first induced signal and the second induced signal have a same transmission speed;

calculating a time difference between receiving of the first induced signal and receiving of the second induced signal, wherein the time difference is linear with the liquid density of the liquid, and is calculated by dividing the distance between the first magnetic unit and the second magnetic unit by the transmission speed of the first induced signal; and calculating the liquid density of the liquid based on the time difference between receiving of the first induced signal and receiving of the second induced signal.

6. The liquid density sensor as claimed in claim 2, wherein the control circuit calculates the liquid level through steps of:

outputting a pulse signal to the sensing line to produce a second induced signal corresponding to the second magnetic unit when the pulse signal passes through the second magnetic unit;

receiving the second induced signal;

calculating a time difference between outputting of the pulse signal and receiving of the second induced signal, wherein the time difference between outputting of the pulse signal and receiving of the second induced signal is linear with the liquid level of the liquid; and calculating the liquid level of the liquid based on the time difference between outputting of the pulse signal and receiving of the second induced signal, wherein the liquid level of the liquid is calculated by multiplying the time difference between outputting of the pulse signal and receiving of the second induced signal by a transmission speed of the second induced signal.

7. The liquid density sensor as claimed in claim 5, wherein the control circuit calculates the liquid level through steps of:

outputting a pulse signal to the sensing line to produce a second induced signal corresponding to the second magnetic unit when the pulse signal passes through the second magnetic unit;

receiving the second induced signal;

calculating a time difference between outputting of the pulse signal and receiving of the second induced signal, wherein the time difference between outputting of the pulse signal and receiving of the second induced signal is linear with the liquid level of the liquid; and calculating the liquid level of the liquid based on the time difference between outputting of the pulse signal and receiving of the second induced signal, wherein the liquid level of the liquid is calculated by multiplying the time difference between outputting of the pulse signal and receiving of the second induced signal by the transmission speed of the second induced signal.

8. The liquid density sensor as claimed in claim 6, wherein the control circuit comprises an external circuit electrically connected to the sensing line and having
- a coil used for receiving the first induced signal and the second induced signal;
- an amplifier electrically connected to the coil to amplify the first induced signal and the second induced signal;
- a comparator electrically connected to the amplifier to obtain the first induced signal and the second induced signal amplified, wherein the comparator converts the first induced signal and the second induced signal from analog forms to digital forms;
- a transistor; and
- a pulse module electrically connected to the transistor and the sensing line for generating and outputting the pulse signal to the sensing line; and an internal circuit electrically connected to the external circuit and comprising
- a receiving module electrically connected to the comparator to receive the first induced signal and the second induced signal;
- a comparing module electrically connected to the receiving module to obtain the first induced signal and the second induced signal,
wherein the comparing module calculates the liquid density of the liquid based on the first induced signal and the second induced signal; and
- an outputting module electrically connected to the transistor and outputting a trigger signal to the transistor for controlling the pulse module to generate the pulse signal.

9. The liquid density sensor as claimed in claim 7, wherein the control circuit comprises an external circuit electrically connected to the sensing line and having
- a coil used for receiving the first induced signal and the second induced signal;
- an amplifier electrically connected to the coil to amplify the first induced signal and the second induced signal;
- a comparator electrically connected to the amplifier to obtain the first induced signal and the second induced signal amplified, wherein the comparator converts the first induced signal and the second induced signal from analog forms to digital forms;
- a transistor; and
- a pulse module electrically connected to the transistor and the sensing line for generating and outputting the pulse signal to the sensing line; and an internal circuit electrically connected to the external circuit and comprising
- a receiving module electrically connected to the comparator to receive the first induced signal and the second induced signal;
- a comparing module electrically connected to the receiving module to obtain the first induced signal and the second induced signal, wherein the comparing module calculates the liquid density of the liquid based on the first induced signal and the second induced signal; and
- an outputting module electrically connected to the transistor and outputting a trigger signal to the transistor for controlling the pulse module to generate the pulse signal.

10. The liquid density sensor as claimed in claim 8, wherein the control circuit further comprises a temperature module, and the internal circuit further comprises a compensation module;

the temperature module comprises
a temperature compensator outputting a temperature signal based on a temperature of the liquid;
a gain augmenter electrically connected to the temperature compensator to obtain and amplify the temperature signal; and
an analog-digital converter electrically connected to the gain augmenter and the compensation module, wherein the analog-digital converter converts the temperature signal from analog form to digital form and outputs the converted temperature signal to the compensation module; and
the compensation module is electrically connected to the comparing module and outputs a compensation signal based on the temperature signal to the comparing module so that the comparing module adjusts the liquid level being calculated according to the compensation signal.

11. The liquid density sensor as claimed in claim 9, wherein the control circuit further comprises a temperature module, and the internal circuit further comprises a compensation module;

the temperature module comprises
a temperature compensator outputting a temperature signal based on a temperature of the liquid;
a gain augmenter electrically connected to the temperature compensator to obtain and amplify the temperature signal; and
an analog-digital converter electrically connected to the gain augmenter and the compensation module, wherein the analog-digital converter converts the temperature signal from analog form to digital form and outputs the converted temperature signal to the compensation module; and
the compensation module is electrically connected to the comparing module and outputs a compensation signal based on the temperature signal to the comparing module so that the comparing module adjusts the liquid level being calculated according to the compensation signal.

12. The liquid density sensor as claimed in claim 8, wherein the control circuit further comprises a temperature module, and the internal circuit further comprises a compensation module;

the temperature module comprises
a cold spot compensator outputting a cold spot signal based on a temperature of the liquid;
a gain augmenter electrically connected to the cold spot compensator to obtain and amplify the cold spot signal;
an analog-digital converter electrically connected to the gain augmenter and the compensation module, wherein the analog-digital converter converts the cold spot signal from analog form to digital form, and outputs the converted cold spot signal to the compensation module; and
the compensation module is electrically connected to the comparing module, wherein the compensation module outputs a compensation signal based on the cold spot signal to the comparing module, so that the comparing module adjusts the liquid level calculated according to the cold spot signal.

13. The liquid density sensor as claimed in claim 9, wherein the control circuit further comprises a temperature module, and the internal circuit further comprises a compensation module;

the temperature module comprises
a cold spot compensator outputting a cold spot signal based on a temperature of the liquid;
a gain augmenter electrically connected to the cold spot compensator to obtain and amplify the cold spot signal;
an analog-digital converter electrically connected to the gain augmenter and the compensation module, wherein the analog-digital converter converts the cold spot signal from analog form to digital form, and outputs the converted cold spot signal to the compensation module; and
the compensation module is electrically connected to the comparing module, wherein the compensation module outputs a compensation signal based on the cold spot signal to the comparing module, so that the comparing module adjusts the liquid level calculated according to the cold spot signal.

14. The liquid density sensor as claimed in claim 8, wherein the control circuit further comprises a temperature module, and the internal circuit further comprises a compensation module;

the temperature module comprises
a temperature compensator outputting a temperature signal based on a temperature of the liquid;
a cold spot compensator outputting a cold spot signal based on the temperature of the liquid;
two gain augmenters electrically connected to the temperature compensator and the cold spot compensator respectively, wherein the two gain augmenters respectively obtain and amplify the temperature signal and the cold spot signal;
two analog-digital converters electrically connected to the two gain augmenters respectively and to the compensation module, wherein the two analog-digital converters respectively convert the temperature signal and the cold spot signal from analog form to digital form, and output the converted temperature signal and the converted cold spot signal to the compensation module; and
the compensation module is electrically connected to the comparing module, wherein the compensation module outputs a compensation signal based on the temperature signal and the cold spot signal, and outputs the compensation signal to the comparing module, and then the comparing module adjusts the liquid level being calculated according to the compensation signal.

15. The liquid density sensor as claimed in claim 9, wherein the control circuit further comprises a temperature module, and the internal circuit further comprises a compensation module;

the temperature module comprises
a temperature compensator outputting a temperature signal based on a temperature of the liquid;
a cold spot compensator outputting a cold spot signal based on the temperature of the liquid;
two gain augmenters electrically connected to the temperature compensator and the cold spot compensator respectively, wherein the two gain augmenters respectively obtain and amplify the temperature signal and the cold spot signal; and
two analog-digital converters electrically connected to the two gain augmenters respectively and to the compensation module, wherein the two analog-digital converters respectively convert the temperature signal and the cold spot signal from analog form to digital form, and output the converted temperature signal and the converted cold spot signal to the compensation module; and the compensation module is electrically connected to the comparing module, wherein the compensation module outputs a compensation signal based on the temperature signal and the cold spot signal, and outputs the compensation signal to the comparing module, and then the comparing module adjusts the liquid level being calculated according to the compensation signal.

16. The liquid density sensor as claimed in claim 1, wherein material of the first magnetic unit and the second magnetic unit comprises nickel (Ni), cobalt (Co) or iron (Fe).

17. The liquid density sensor as claimed in claim 1, wherein a shape of the first magnetic unit and the second magnetic unit is annular, cylindrical, cube or irregular.

18. The liquid density sensor as claimed in claim 1, wherein the floating ball is made of a foam material.

\* \* \* \* \*